(12) United States Patent
Kuczynski et al.

(10) Patent No.: US 6,361,795 B1
(45) Date of Patent: Mar. 26, 2002

(54) METHOD FOR LOWERING BLOOD GLUCOSE

(75) Inventors: Anthony L. Kuczynski, Mountain View; Atul Devolatt Ayer; Patrick S. L. Wong, both of Palo Alto, all of CA (US)

(73) Assignee: Alza Corporation, Mountain View, CA (US)

( * ) Notice: Subject to any disclaimer, the term of this patent is extended or adjusted under 35 U.S.C. 154(b) by 0 days.

(21) Appl. No.: 08/180,409

(22) Filed: Jan. 11, 1994

Related U.S. Application Data

(60) Continuation-in-part of application No. 07/650,822, filed on Jan. 22, 1991, now Pat. No. 5,545,413, which is a division of application No. 07/402,314, filed on Sep. 5, 1989, now Pat. No. 5,024,843.

(51) Int. Cl.[7] .............................. A61K 9/22; A61K 9/26; A61P 3/10
(52) U.S. Cl. ...................... 424/473; 514/255; 514/866
(58) Field of Search ................. 424/499, 494, 424/475, 473, 424, 426, 78.1; 514/255, 866

(56) References Cited

U.S. PATENT DOCUMENTS

| | | | |
|---|---|---|---|
| 2,799,241 A | 7/1957 | Wurster | 118/24 |
| 2,909,462 A | 10/1959 | Warfield et al. | 167/56 |
| 3,845,770 A | 11/1974 | Theeuwes et al. | 128/260 |
| 3,916,899 A | 11/1975 | Theeuwes et al. | 128/260 |
| 4,016,880 A | 4/1977 | Theeuwes et al. | 128/260 |
| 4,063,064 A | 12/1977 | Saunders et al. | 219/121 L |
| 4,088,864 A | 5/1978 | Theeuwes et al. | 219/121 LM |
| 4,200,098 A | 4/1980 | Ayer et al. | 128/260 |
| 4,285,987 A | 8/1981 | Ayer et al. | 427/3 |
| 4,627,851 A | 12/1986 | Wong et al. | 424/473 |
| 4,673,405 A | 6/1987 | Guittard et al. | 424/473 |
| 4,708,868 A | 11/1987 | Bricul et al. | 424/80 |
| 4,792,448 A | * 12/1988 | Ranade | 424/438 |
| 4,851,232 A | 7/1989 | Urquehart et al. | 424/469 |
| 4,902,514 A | 2/1990 | Barclay et al. | 424/473 |
| 5,019,396 A | 5/1991 | Ayer et al. | 424/473 |
| 5,024,843 A | 6/1991 | Kuczynski et al. | 424/499 |
| 5,028,434 A | 7/1991 | Barclay et al. | 424/473 |

OTHER PUBLICATIONS

Martindale, *The Extra Pharmacopoeia*, 29th Ed. (1989) p 390.
AHF *Drug Information*, (1989) pp 1741–1745.
*J. Am. Phar. Assoc.*, Sci. Ed., vol. 48 (1959) pp 451–459.
*J. Am. Phar. Assoc.*, Sci. Ed., vol. 49 (1960) pp 82–84.
Remington's *Pharmaceutical Sciences*, 14th Ed., (1970) pp 1626–1678.

\* cited by examiner

*Primary Examiner*—Edward J. Webman
(74) *Attorney, Agent, or Firm*—D. Byron Miller; Robert R. Neller

(57) ABSTRACT

The invention disclosed comprises a method for administering the antidiabetic drug glipizide to a patient in need of glipizide in need of antidiabetic therapy.

2 Claims, 2 Drawing Sheets

METHOD FOR LOWERING BLOOD GLUCOSE

CROSS-REFERENCE TO CO-PENDING APPLICATION

Figure 1:
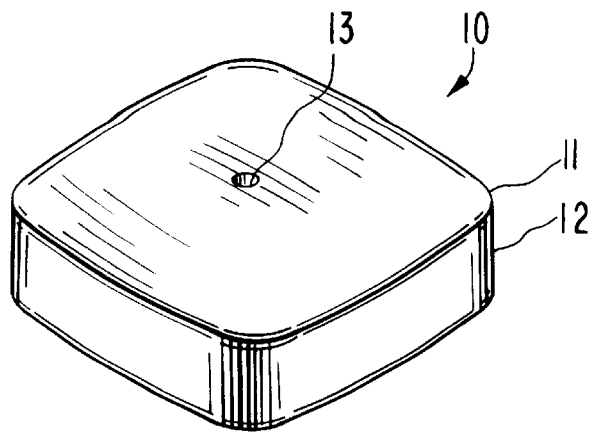

This application is a continuation-in-part of U.S. Appln. Ser. No. 07/650,822 filed Jan. 22, 1991, now U.S. Pat. 5,545,413 which Ser. No. 07/650,822 is a division of U.S. Appln. Ser. No. 07/402,314, filed Sep. 5, 1989 which Ser. No. 07/402,314 now is U.S. Pat. No. 5,024,843 issued Jun. 18, 1991, and was with U.S. Ser. No. 07/652,717 now U.S. Pat. No. 5,091,190 issued Feb. 25, 1992, and benefit of these filing dates is claimed herein.

DISCLOSURE OF TECHNICAL FIELD

This invention pertains to dosage forms comprising the drug glipizide. The invention relates also to compositions comprising glipizide, and the invention concerns additionally a method for administering glipizide to a patient in need of glipizide therapy.

DISCLOSURE OF BACKGROUND OF THE INVENTION

A clinical need exists for a dosage form and for a method for delivering an oral blood-glucose lowering drug to a patient needing this therapy. Glipizide is an oral blood-glucose lowering drug and it is indicated for the control of hyperglycemia and its associated symptomatology in patients with non-insulin dependent diabetes mellitus. Glipizide is useful therapeutically as an oral hypoglycemic drug because it stimulates insulin secretion from the beta cells of pancreatic-islet tissue, it increases the concentration of insulin in the pancreatic vein, and because it exhibits extrapancreatic action such as the ability to increase the number of insulin receptors.

Glipizide is known chemically as N-[2-[4-[[[(cyclohexylamino) carbonyl]amino]sulfonyl]phenyl]ethyl]-5-methylpyrazinecarboxamide. Glipizide is a white, odorless powder with a pKa of 5.9, and it is insoluble in both water and alcohol. These physical and chemical properties of glipizide do not lend the drug to formulation into a dosage form, and these properties do not lead to a method, that in both instances that can administer glipizide at a controlled and known rate per unit time to produce the intended therapy. The properties of glipizide are disclosed in *Martindale The Extra Pharmacopoeia*, 29th Ed., p 390, (1989); and, *AHFS Drug Information*, pp 1741–45, (1989).

In the light of the above presentation, it will be appreciated by those versed in the medical and in this pharmaceutical dispensing art to which this invention pertains, that a pressing need exists for dosage forms that can deliver the valuable drug glipizide in a rate-controlled dose to a patient in clinical need of blood-glucose lowering therapy. The pressing need exists also for an oral dosage form and for a method of therapy that can deliver glipizide at a controlled rate in a substantially constant dose per unit time for its beneficial therapeutic effects, and remain substantially independent of the changing environment of the gastrointestinal tract. It will be appreciated further by those skilled in the dispensing art, that if such a novel and unique dosage form and method is made available that can administer glipizide in a rate-controlled dose over time, and simultaneously provide a method of blood-glucose lowering therapy, the dosage form and the accompanying method would represent an advancement and a valuable contribution to the medical art.

DISCLOSURE OF OBJECTS OF THE INVENTION

Accordingly, in view of the above presentation, it is an immediate object of this invention to provide a dosage form for delivering glipizide in a rate controlled amount, and which dosage form substantially overcomes the deficiencies and omissions associated with the prior art.

Another object of the present invention is to provide a dosage form for orally administering glipizide in a rate-controlled dose for blood-glucose lowering therapy.

Another object of the invention is to provide a pharmaceutical dosage form that makes available controlled and sustained glipizide therapeutic activity to a patient in need of glipizide therapy.

Another object of the invention is to provide a novel dosage form manufactured as an osmotic, diffusional, bioerodible or ion-exchange device that can administer glipizide to a biological receptor site to produce the desired glipizide pharmacological effects.

Another object of the present invention is to provide a dosage form manufactured as an osmotic, diffusional, bioerodible, or ion-exchange dosage form that maintains glipizide in the dosage form until released from the dosage form, thereby substantially reducing and/or substantially eliminating the unwanted influences of the gastrointestinal environment of use and still provide controlled administration of glipizide over time.

Another object of the present invention is to provide a dosage form that can deliver the substantially aqueous insoluble drug glipizide at a controlled and beneficial known rate over time.

Another object of the present invention is to provide a dosage form adapted for the oral administration of glipizide and which dosage form comprise a first composition and a contacting second composition that operate in combination for the controlled administration of glipizide.

Another object of the present invention is to provide a complete pharmaceutical glipizide regimen comprising a composition comprising glipizide that can be dispensed from a drug delivery dosage form, the use of which requires intervention only for initiation and possibly for termination of the regimen.

Another object of the invention is to provide a method for treating hyperglycemia by orally administering glipizide in a rate-controlled dose per unit time to a warm-blooded animal in need of hyperglycemia therapy.

Another object of the invention is to provide a method that engages osmotic, diffusional, bioerodible, or ion-exchange delivery for administering glipizide in a therapeutic dose per unit time or an extended time to a human patient in need of glipizide therapy.

Other objects, features and advantages of this invention will be more apparent to those versed in the dispensing arts from the following detailed specification, taken in conjunction with the drawings and the accompanying claims.

BRIEF DISCLOSURE OF THE DRAWINGS

Figure 2:
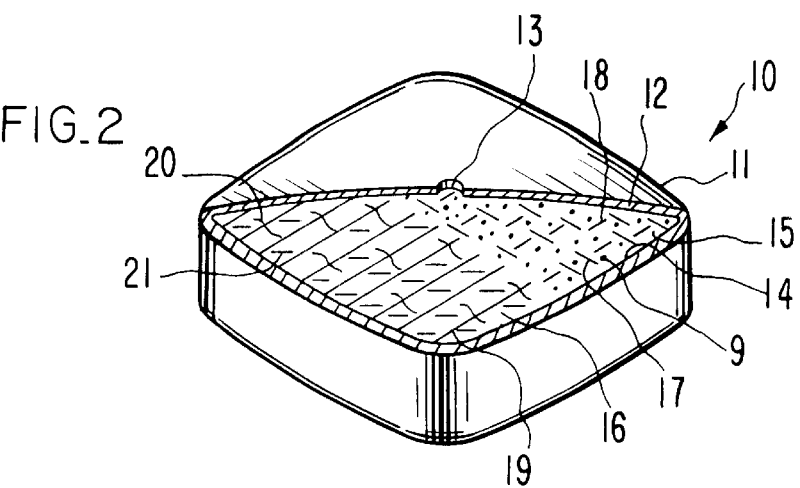
Figure 3:
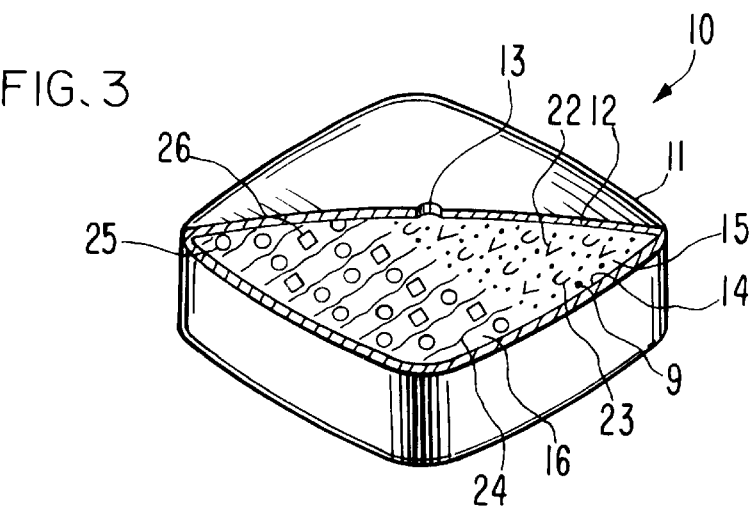
Figure 4:
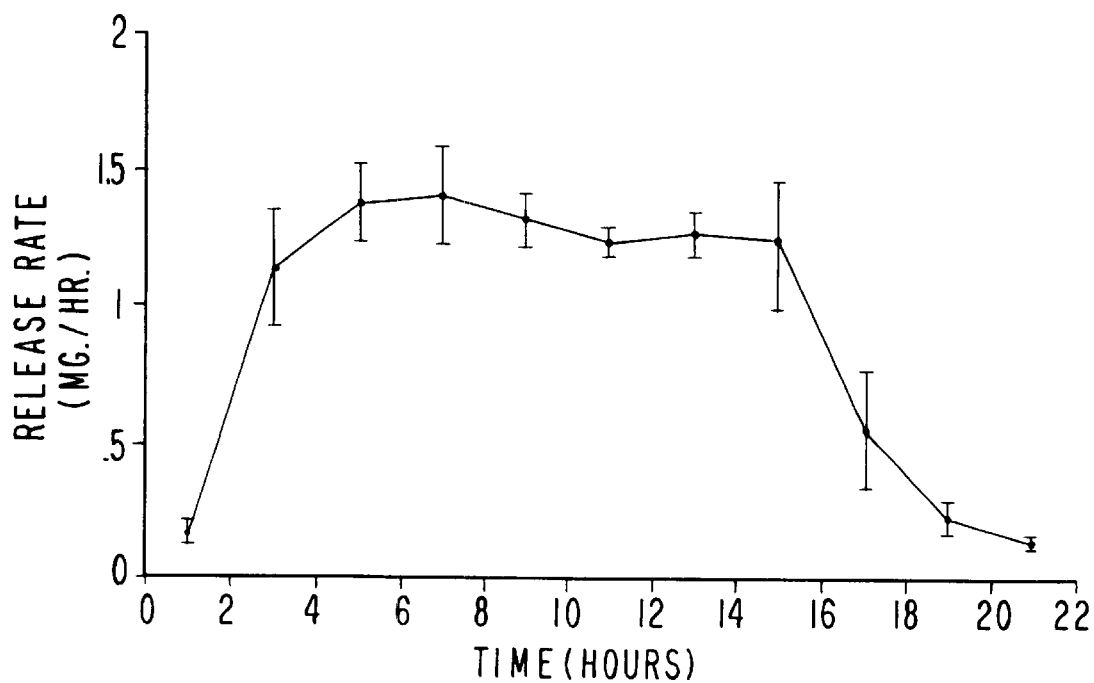
Figure 5:
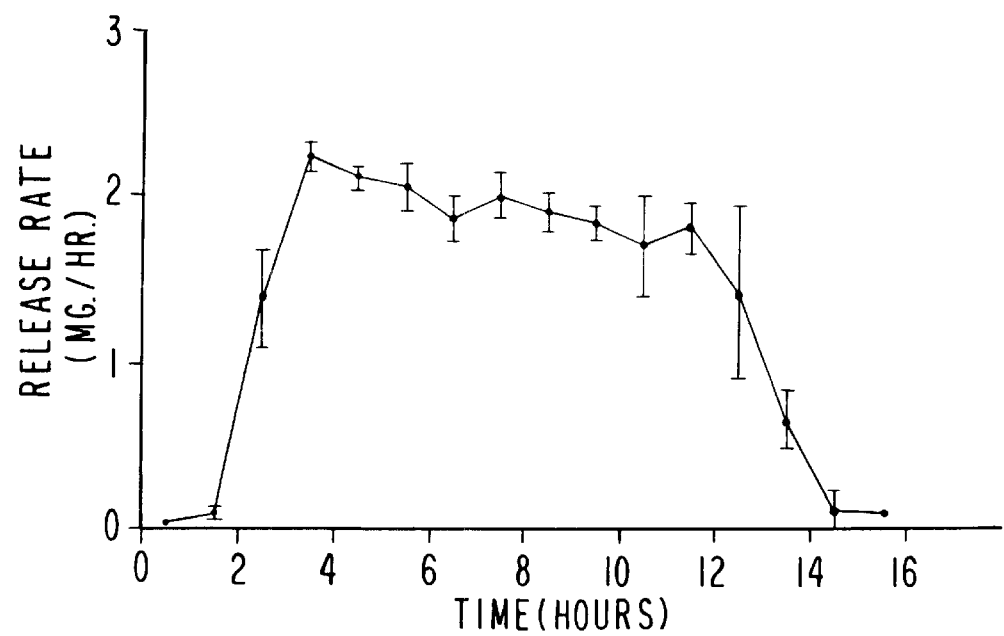

In the drawings, which are not drawn to scale, but are set forth to illustrate various embodiments of the invention, the drawing figures are as follows:

Drawing FIG. 1 is a view of one dosage form provided by the invention designed and shaped for orally administering glipizide to the gastrointestinal tract of a warm-blooded animal, including humans;

Drawing FIG. 2 is an opened view of a dosage form of drawing FIG. 1 illustrating the structure of the dosage form comprising glipizide;

Drawing FIG. 3 is an opened view of the dosage form of drawing FIG. 1 depicting a different internal structure embodiment provided by the invention;

Drawing FIG. 4 is a graph that depicts the release rate pattern from one embodiment of the dosage form provided by the method of the invention that administers glipizide at a rate-controlled by the dosage form over an extended period of therapy; and, Drawing FIG. 5 is a graph that depicts the release rate pattern for a different embodiment of the dosage form provided by the invention, wherein the glipizide is administered by a method employing an osmotic, diffusional, bioerodible, or ion-exchange dosage form.

In the drawing figures and in the specification like parts in related drawing figures are identified by like numbers. The terms appearing earlier in the specification and in the description of the drawings, as well as embodiments thereof, are further described elsewhere in the disclosure.

DETAILED DISCLOSURE OF THE DRAWING FIGURES

Turning now to the drawing figures in detail, which drawing figures are examples of the dosage forms provided by this invention, and which examples are not to be construed as limiting, one example of the dosage form is illustrated in drawing FIG. 1 and designated by the numeral 10. In drawing FIG. 1, dosage form 10 comprises a body 11, which body member 11 comprises a wall 12 that surrounds and encloses an internal compartment, not seen in drawing FIG. 1. Dosage form 10 comprises at least one exit means 13 for connecting the interior of dosage form 10 with the exterior environment of use.

In drawing FIG. 2, dosage form 10 is seen in opened view. In drawing FIG. 2, dosage form 10 comprises a body member 11 comprising wall 12, which wall surrounds and defines an internal compartment 14. Wall 12 comprises at least one exit means 13 that connects internal compartment 14 with the exterior of dosage form 10. Dosage form 10 can comprise more than one exit means 13. Wall 12 of dosage form 10 comprises in total, or in at least a part, a composition that is permeable to the passage of an exterior fluid present in the environment, and wall 12 is substantially impermeable to the passage of glipizide and other ingredients present in compartment 14. The composition comprising wall 12 is semipermeable, it is substantially inert, and wall 12 maintains its physical and chemical integrity during the dispensing life of glipizide from dosage form 10. The phrase, "keeps its physical and chemical integrity," means wall 12 does not lose its structure, and it does not change chemically during the glipizide dispensing life of dosage form 10.

Wall 12, in a present embodiment, comprises 60 weight percent (wt %) to 100 weight percent of a composition comprising a cellulose polymer. The cellulose polymer comprises a member selected from the group consisting of a cellulose ester, cellulose ether, cellulose ester-ether, cellulose acylate, cellulose diacylate, cellulose triacylate, cellulose acetate, cellulose diacetate, and cellulose triacetate. Wall 12, in another manufacture, comprises from 0 weight percent to 25 weight percent of a member selected from the group consisting of hydroxyalkylcellulose, hydroxypropylalkylcellulose, hydroxypropylcellulose, and hydroxypropylmethylcellulose, and from 0 to 20 weight percent of polyethylene glycol, with the total amount of all wall-forming components comprising wall 12 equal to 100 weight percent.

Internal compartment 14 in one dosage form comprises an internal glipizide lamina 15, which glipizide lamina can be defined as glipizide composition 15. Internal compartment 14 also comprises an internal displacement lamina 16, which displacement lamina can be defined as displacement composition 16. The glipizide lamina 15 and the displacement lamina 16 initially are in laminar arrangement and they cooperate with each other and with dosage form 10 for the effective delivery of glipizide from dosage form 10.

The glipizide composition 15, in a present embodiment, as seen in FIG. 2, comprises about 2.0 mg to 750 mg of glipizide identified by dots 9; from 100 mg to 320 mg of a polyethylene oxide comprising 80,000 to 350,000 molecular weight identified by dashes 17; from 5 mg to 50 mg of hydroxypropylmethylcellulose comprising a 9,200 to 22,000 molecular weight identified by vertical lines 18; and from 0 mg to 7.5 mg of a lubricant such as stearic acid, magnesium stearate, and the like.

The displacement lamina 16, as seen in drawing FIG. 2, comprises 70 mg to 125 mg of a polyethylene oxide comprising a 4,000,000 to 8,000,000 molecular weight identified as lines 19; from 20 mg to 50 mg of an osmagent selected from the group consisting of sodium chloride and potassium chloride identified by wavy line 20; and from 5 mg to 15 mg of a hydroxypropylmethylcellulose having a 9,000 to 25,000 molecular weight identified by vertical slashes 21. Displacement lamina 16 optionally comprises from 0.1 mg to 5 mg of ferric oxide and from 0.01 mg to 5 mg of a lubricant such as magnesium stearate or stearic acid.

Dosage form 10, in another manufacture the internal compartment 14 comprises a homogenous composition comprising 2.0 mg to 750 mg of glipizide and an osmagent that exhibits an osmotic pressure gradient across semipermeable wall 12 against an external aqueous or biological fluid. The osmagents are known also as osmotically effective solute and as osmotically effective compound. The amount of osmagent is 1 mg to 350 mg for providing the composition comprising glipizide. The osmagent operable for the purpose of this dosage form comprises a member selected from the group consisting of water-soluble inorganic salts, water soluble sugars, organic osmagents and organic salts. Representative osmagents include sodium chloride, potassium chloride, potassium acid phosphate, tartaric acid, citric acid, raffinose, magnesium sulfate, magnesium chloride, urea, inositol, sucrose, glucose, and sorbitol. Osmagents are known in U.S. Pat. No. 4,783,332.

Drawing FIG. 3 depicts in opened section another dosage form 10 provided by the invention. In drawing FIG. 3, dosage form 10 comprises a body 11, a wall 12, which wall 12 surrounds an internal compartment 14 with an exit passageway 13 in wall 12. Internal compartment 14, in this dosage form, comprises an internal glipizide lamina 15, which glipizide lamina 15 comprises 2 mg to 225 mg of aqueous insoluble drug glipizide identified by dots 9; from 100 mg to 250 mg of a hydroxypropylcellulose comprising a 40,000 to 80,000 molecular weight identified by angle 22; and from 40 mg to 70 mg of a polyvinylpyrrolidone comprising a 30,000 to 70,000 molecular weight and identified by half circle 23. Internal compartment 14 comprises a displacement lamina 16 comprising 30 mg to 150 mg of sodium carboxymethylcellulose having 200,000 to 1,000,000 molecular weight identified by wavy lines 24; from 20 mg to 70 mg of an osmagent selected from the group consisting of osmogent sodium chloride, and potassium chloride identified by circle 25; and from 0.5 mg to 10 mg of a hydroxypropylmethylcellulose comprising a 9,200 to 22,000 molecular weight identified by squares 26. Displacement lamina 16 optionally comprises from 0 mg to 5 mg of ferric oxide and optionally 0 mg to 7 mg of a lubricant.

The expression, "exit means 13," as used herein, comprises means and methods suitable for the controlled metered release of glipizide 9 from compartment 14 of dosage form 10. The exit means 13 comprises at least one passageway, orifice, or the like, through wall 12 for communication with glipizide 9 in compartment 14. The expression, "at least one passageway," includes aperture, orifice, bore, pore, or porous element through which glipizide can be released, or hollow fiber, capillary tube, porous overlay, porous insert, and the like. The expression also includes a material that erodes or is fluid-leached from wall 12 in a fluid environment of use to produce at least one pore-passageway of governed release rate pore-size in wall 12. Representative materials suitable for forming at least one passageway, or a multiplicity of passageways, comprise an erodible polyglycolic acid, or a polylactic acid member in wall 12, a gelatinous filament, polyvinyl alcohol, leachable materials such as a fluid removable pore forming polysaccharide, salt, oxide, polyol, or the like. A passageway or a plurality of passageways can be formed by leaching a material such as sorbitol, lactose, or the like, from wall 12. The passageway can have any shape such as round, triangular, square, elliptical, and the like, for assisting in the metered release of glipizide 9 from dosage form 10. Dosage form 10 can be constructed with one or more passageways in spaced apart relations, or more than one passageway on a single surface of dosage form 10. Passageways and equipment for forming passageways are disclosed in U.S. Pat. No. 3,845,770 issued November 1974 to Theeuwes et al; U.S. Pat. No. 3,916,899 issued November 1975 to Theeuwes et al; U.S. Pat. No. 4,016,880 issued April 1977 to Theeuwes et al; U.S. Pat. No. 4,063,064 issued December 1977 to Saunders et al; U.S. Pat. No. 4,088,864 issued May 1978 to Theeuwes et al; and, passageways formed by leaching are disclosed in U.S. Pat. Nos. 4,200,098 issued April 1980 to Ayer et al; U.S. Pat. No. 4,235,236 issued November 1980 to Theeuwes; and, U.S. Pat. No. 4,285,987 issued to Ayer et al.

Dosage form 10 used for the purpose of the invention includes also dosage forms 10 that mediate the efficiency of glipizide by imparting enhanced therapy from administering glipizide by the method of the invention. Dosage forms 10 contemplated by the invention also comprise a dosage form selected from the group consisting of a bioerodiable-mediated dosage form, diffusion-mediated dosage form and ion-exchange mediated dosage form.

The bioerable-mediated dosage form 10 comprises a bioerodable polymer matrix containing glipizide. Dosage form 10 provides a mediated-release rate of glipizide delivered to a glipizide-drug receptor as the polymer matrix bioerodes at a release-rate controlled by the bioeroding matrix over time. Bioerodable polymers for forming the dosage form containing glipizide include a member selected from the group consisting of poly(ester) poly(amine), poly(lactide), poly(glycolide), poly(lactide-co-glycolide), poly(caprolactone), poly(hydroxybutyric acid), poly(orthoester), poly(orthocarbonate), poly(acetal), poly(carbohydrate), poly(peptide), and poly(dehydropyran). The bioerodable-mediated dosage form comprises 2.0 mg to 750 mg of glipizide compounded with the bioerodable polymer.

The diffusion-mediated dosage form 10 comprises a membrane-controlled diffusion that permits diffusion of glipizide through a polymer membrane or diffusion of glipizide through a porous polymer membrane. The diffusion mediated dosage form 10 structurally includes a polymer matrix with glipizide thereon that is released by the process of diffusion, and a reservoir or depot polymer dosage form with glipizide in the reservoir that is released therefrom by a process of diffusion through a contacting polymer rate-governing membrane. Representative of polymers for providing a diffusional dosage form comprise a member selected from the group consisting of poly(olefin), poly(vinyl), poly(carbohydrate), poly(peptides), poly(condensation), poly(rubber), and poly(silicon). Representative of specific polymers are a member selected from the group consisting of poly(ethylene), poly(propylene), copoly (ethylene-vinylacetate), poly(isobutylethylene), poly(vinylacetate), cross-linked poly(vinyl-alcohol), poly(methyacrylate), poly(amide), poly(ester), poly(ether), and poly(silicone).

The ion-exchange mediated dosage form comprises water-insoluble-crosslinked polymers with glipizide bound to the resin. The glipizide is released at a rate controlled by the glipizide-resin complex by the ionic environment within the gastrointestinal tract. The ion-exchanged mediated dosage form comprises cation-exchange resins containing electronegative charges and anion-exchange resins containing electropositive charges. The cation-exchange resins include strong-acid weak-acid resins as with sulfonic acid, carboxylic acid, and phosphonic acid, and the anion-exchange resins include strong-base and weak-base resins as with quaternary ammonium, secondary amine, tertiary amine aromatic, and tertiary amine aliphatic resins. Specific examples of ion-exchange resins mention is made of acidic ion-exchange resins mention is made of acidic ion-exchange resins such as Amberlite IR-120, basic ion-exchange resins such as Amberlite IRA-400, and weak basic ion-exchange resins such as Amberlite IR-45.

PROCEDURES FOR MANUFACTURING THE DOSAGE FORM

Dosage form 10 of this invention is manufactured by standard techniques. For example, in one manufacture the drug glipizide is mixed with other composition-forming ingredients and the mix then pressed into a solid lamina possessing dimensions that correspond to the internal dimensions of the compartment space adjacent to the passageway. In another embodiment the beneficial drug glipizide and other composition forming ingredients and a solvent are mixed into a solid, or into a semisolid, by conventional methods such as ballmilling, calendering, stirring, or rollmilling, and then pressed into a preselected lamina forming shape. Next, a lamina composition comprising the osmopolymer and the osmagent are placed in contact with the lamina comprising the beneficial drug glipizide, and the two lamina comprising the laminate are surrounded with a semipermeable wall. The lamination of the glipizide composition and the osmopolymer displacement composition can be accomplished by using a two-layer tablet press technique. The wall can be applied by molding, spraying, or dipping the pressed shapes into wall-forming formulations. Another preferred technique that can be used for applying the wall is the air suspension coating procedure. This procedure consists in suspending and tumbling the two layered laminate in a current of air until the wall forming composition surrounds the laminate. The air suspension procedure is described in U.S. Pat. No. 2,799,241; in *J. Pharm. Assoc., Sci. Ed.*, Vol. 48 pp 451–59 (1959); and ibid, Vol. 49, pp 82–84, (1960). Other standard manufacturing procedures are described in *Modern Plastics Encyclopedia*, Vol. 46, pp 62–70, (1969); and in *Pharmaceutical Sciences*, by Remington, 14th Ed., pp 1626–1978, (1970), published by Mack Publishing Co., Easton, Pa.

The bioerodable-mediated dosage form is provided by dispensing or mixing the drug into the bioerodible polymer by blending by spatula, in a v-shaped blender, or on a three-roll mill. The blend is heated until pliable to thoroughly mix the polymer and drug to yield the loaded polymer. After the blend cools to room temperature, the blend can be molded into a preselected design and shaped and sized for therapeutic use.

A diffusion-mediated dosage form is fabricated by mixing the drug in particulate form with a polymer, which can be in solid, semi-solid or liquid form, and distributed therethrough by ballmilling, calendering, stirring, or shaking. Monomers or prepolymers can be used to form the reservoir, or a matrix formed in situ. A reservoir, or matrix comprising drug distributed therethrough can be formed into a solid shape by molding, casting, pressing, extruding or drawing. A polymeric membrane is applied to a reservoir by wrapping, laminating or heat shrinking, or the polymer membrane can be formed by drawing or stamping the polymer thereto. A preformed shape of the polymer, such as tube can be filled with drug and seal to form a closed diffusional form. A polymer membrane, or matrix can be converted to a solid by curing to yield the desired dosage form.

An ion-exchanged mediated dosage form where the absorption of the drug onto the ion-exchange resin to form a drug resin complex, is provided by mixing the drug with an aqueous suspension of the resin and the complex is then dried. Absorption of the drug onto the resin is detected by a change in the pH of the reaction medium. The ion-exchange resin drug complex can be solvated by the use of solvating agents such as polyethylene glycol to enable this complex to release the drug at a controlled-rate over an extended period of drug therapy.

Exemplary solvents suitable for manufacturing the wall, laminate, compositions, comprise inert inorganic and organic solvents that do not adversely affect the final wall and the final laminates. The solvents broadly comprise a member selected from the group consisting of aqueous solvents, alcohols, ketones, esters, ethers, aliphatic hydrocarbons, halogenated solvents, cycloaliphatics, aromatics, heterocyclic solvents, and mixtures thereof. Typical solvents comprise acetone, diacetone, alcohol, methanol, ethanol, isopropyl alcohol, butyl alcohol, methyl acetate, ethyl acetate, isopropyl acetate, n-butyl acetate methyl isobutyl ketone, methylpropyl ketone, n-hexane, n-heptane, ethylene glycol monethyl ether, ethylene glycol monethyl acetate, methylene dichloride, ethylene dichloride, propylene dichloride, acetone and water, acetone and methanol, acetone and ethyl alcohol, methylene dichloride and methanol, ethylene dichloride and methanol, and the like.

DETAILED DISCLOSURE OF EXAMPLES OF THE INVENTION

The following examples are merely illustrative of the present invention, and they should not be considered as limiting the scope of this invention in any way, as these examples and other equivalents thereof will become apparent to those versed in the art in the light of the present disclosure, the drawings and the accompanying claims.

EXAMPLE 1

An oral dosage form, adapted, designed and shaped as drug delivery system for admittance into the gastrointestinal tract of a patient in need of glipizide is manufactured as follows: first, 369 g of pharmaceutically acceptable hydroxypropylcellulose comprising a 60,000 average molecular weight is passed through a 20 mesh screen, followed by passing through a 40 mesh screen 162 g of pharmaceutically acceptable polyvinylpyrrolidone comprising a 40,000 average molecular weight. Next, the two screened ingredients are blended with 66 g of glipizide to form a homogeneous blend. The blend is suspended in a fluidized bed and sprayed with an atomized spray comprising an ethanol:water (70:30 vol:vol) solution until granules are formed of the three ingredients. The freshly prepared granules then are passed through a 20 mesh screen. Finally, the screened granulation is mixed with 3 g of magnesium stearate in a rollermill for 5 minutes.

Next, a separate hydrogel granulation is prepared as follows: first, 389 g of pharmaceutically acceptable sodium carboxymethylcellulose having 700,000 molecular weight, 174 g of sodium chloride, 30 g of pharmaceutically acceptable hydroxypropylmethylcellulose comprising a 11,200 molecular weight and 6 g of ferric oxide separately are screened through a 40 mesh screen. Then, all the screened ingredients are mixed to produce a homogeneous blend. Next, 300 ml of denatured anhydrous ethanol is added slowly to the blend with continuous mixing for about 5 minutes. The freshly prepared wet granulation is screened through a 20 mesh screen, allowed to dry at room temperature for 16 hours, and again passed through a 20 mesh screen. The screened granulation is mixed with 1.5 g of magnesium stearate in a rollermill for about 5 minutes.

Next, the glipizide granulation, and the hydrogel granulation are compressed into a bilaminate tablet arrangement. First, 200 mg of the glipizide composition is added to a 0.375 inch (9.5 mm) punch and tamped, then, 140 mg of the hydrogel granulation is added to the punch and the two laminae are pressed into a solid, contacting arrangement.

Next, the bilaminate is coated with a semipermeable wall. The semipermeable wall-forming composition comprises 93% cellulose acetate having a 39.8% acetyl content, and 7% polyethylene glycol having a 3350 molecular weight. The wall-forming composition is dissolved in a cosolvent comprising acetone: water (90:10 wt:wt) to make a 4% solids solution. The wall-forming composition is sprayed onto and around the bilaminate in an Aeromatic® Air Suspension Coater.

Then, a 25 mil (0.635 mm) exit orifice is mechanically drilled on the glipizide side of the osmotic dosage form. The residual solvent is removed by drying the osmotic system for 48 hours at 50° C. and 50% humidity. The osmotic systems are dried for 1 hour at 50° C. to remove excess moisture. Attached drawing FIG. 4 shows the in vitro release rate profile for glipizide from the finished osmotic system as released in distilled water. The error bars represent the standard deviation added to and subtracted from the mean of five osmotic delivery system. An osmotic dosage form provided by the invention comprises 11 wt % glipizide, 61.50 wt % hydroxypropyl- cellulose of 60,000 molecular weight, 27.0 wt % polyvinylpyrrolidone of 40,000 molecular weight, 0.5% magnesium stearate in the glipizide composition; 64.8 wt % sodium carboxymethylcellulose of 700,000 molecular weight, 29 wt % sodium chloride, 5 wt % hydroxypropylmethylcellulose of 11,200 molecular weight and 1.0 wt % ferric oxide, 0.2% magnesium stearate in the hydrogel composition; and, 93.0 wt % cellulose acetate having a 39.8% acetyl content, and 7.0 wt % polyethylene glycol having a 3350 molecular weight in the semipermeable wall formulation.

EXAMPLE 2

A dosage form adapted, designed and shaped as an osmotic delivery system is manufactured as follows: first, a glipizide composition is provided by blending together into a homogeneous blend 478 g of pharmaceutically acceptable polyethylene oxide comprising a 200,000 molecular weight, 66 g of glipizide and 54 g of pharmaceutically acceptable hydroxypropylmethylcellulose comprising a 11,200 molecular weight. Then, 425 ml of denatured anhydrous ethanol is added slowly with continuous mixing over 5 minutes. The freshly prepared wet granulation is screened through a 20 mesh screen through a 20 mesh screen, dried at room temperature for 16 hours, and again screened through a 20 mesh screen. Finally, the screened granulation is mixed with 1.5 g of magnesium stearate in a rollermill for 5 minutes.

Next, a hydrogel composition is prepared as follows: first, 412.5 g of pharmaceutically acceptable polyethylene oxide comprising a 7,500,000 molecular weight, 150 g of sodium chloride and 6 g of ferric oxide separately are screened through a 40 mesh screen. Then, all the screened ingredients are mixed with 30 g of hydroxypropylmethylcellulose comprising a 11,200 molecular weight to produce a homogeneous blend. Next, 300 mg of denatured anhydrous alcohol is added slowly to the blend with continuous mixing for 5 minutes. The freshly prepared wet granulation is passed through a 20 mesh screen, allowed to dry at room temperature for 16 hours, and again passed through a 20 mesh screen. The screened granulation is mixed with 1.5 g of magnesium stearate in a rollermill for 5 minutes.

Next, the glipizide composition and the hydrogel composition are compressed into bilaminate tablets. First, 200 mg of the glipizide is added to a 0.375 inch (9.5 mm) punch and tamped, then, 140 mg of the hydrogel composition is added and the laminae are pressed under a pressure head of 2 tons into a contacting laminated arrangement.

Then, the bilaminate arrangements are coated with a semipermeable wall. The wall forming composition comprises 93% cellulose acetate having a 39.8% acetyl content, and 7% polyethylene glycol having a molecular weight of 3350. The wall-forming composition is dissolved in an acetone:water (90:10 wt:wt) cosolvent to make a 4% solids solution. The wall forming composition is sprayed onto and around the bilaminate in an Aeromatic® Air Suspension Coater.

Next, a 25 mil (0.635 mm) exit passageway is mechanically drilled through the semipermeable wall to connect the glipizide drug lamina with the exterior of the dosage system. The residual solvent is removed by drying for 48 hours at 50° C. and 50% humidity. Next, the osmotic systems are dried for 1 hour at 50° C. to remove excess moisture. The dosage form produced by this manufacture provides a glipizide composition comprising 11 wt % glipizide, 79.7 wt % polyethylene oxide of 200,000 molecular weight, 9 wt % hydroxypropylmethylcellulose of 11,200 molecular weight, and 0.3 wt % magnesium stearate; a hydrogel composition comprising 68.8 wt % polyethylene oxide comprising a 7,500,000 molecular weight, 25 wt % sodium chloride, 5 wt % hydroxypropylmethylcellulose, 1.0 wt % ferric oxide and 0.2 wt % magnesium stearate; and a semipermeable wall comprising 93 wt % cellulose acetate comprising a 39.8% acetyl content, and 7.0 wt % polyethylene glycol comprising a 3350 molecular weight.

Accompanying drawing FIG. 5 depicts the in vitro release rate profile of glipizide released from the final dosage form for four dosage forms. The error bars represent the standard deviation added to and subtracted from the mean of the dosage form.

EXAMPLE 3

A therapeutic dosage form for administering glipizide is made as follows: first, 125 mg of glipizide is sieved through a No. 40 mesh sieve and dry mixed with 125 mg of sorbitol, 100 mg of hydroxypropylmethylcellulose, 25 mg of cellulose and 5 mg of sodium chloride. Then, the mixture is blended with ethanol into a uniform, doughy mass. The resulting dough is passed through a No. 20 mesh sieve to form damp granules. The granules are air dried overnight, then re-passed through a No. 20 mesh sieve. Next, the sieve composition is compressed into a 15 mm oval tablet tooling at 2 tons pressure. The resulting compressed cores comprising the homogenous glipizide formulation is coated with about 50 mg of a 50/50 wt % mixture of cellulose acetate and polyethylene glycol deposited from a 95/5 wt % acetone and water solution. Then, the coated dosage form is air dried overnight, and an exit port drilled through the semipermeable wall connecting the exterior of the dosage form with the glipizide.

EXAMPLE 4

A diffusion-mediated dosage form is prepared as follows: first 75 mg of glipizide is mixed with 50 parts of poly (dimethylsiloxane) and 1 part of silicone oil, and to this well-stirred mixture is added 0.15 parts by weight of stannous actoate curing catalyst, and the mixture injected into a poly(ethylene) tube and cured for 30 minutes. Then, the cured reservoir is removed from the poly(ethylene) tube and placed inside a rate-controlling copoly(ethylene-vinyl acetate) tube and sealed with poly(tetrafluoroethylene) plugs and cyanoacrylate adhesive. The dosage form releases glipizide over 24 hours.

EXAMPLE 5

A bioerodible delivery system is prepared by heating poly(2.2-dioxotrans-1, 4-cyclohexane dimethylene tetrahydrofuran) to 120°C. and blending therein glipizide and dispersed with mixing for 5 minutes into the hot melt of the polymer. After cooling to room temperature, the glipizide-bioerodable polymer formulation is pressed into a film under 10,000 psi for 5 minutes and placed inside a capsule, and on oral administration the dosage form releases glipizide at a rate controlled over time.

DISCLOSURE OF A METHOD OF USING THE INVENTION

The invention pertains further to a method for delivering the beneficial drug glipizide orally at a controlled rate to a warm blooded animal in need of glipizide therapy by a method selected from the group consisting of osmotic, diffusion, bioerosion and ion-exchange. One method provided by the invention comprises the steps of: (A) admitting into the warm-blooded animal a dosage form comprising: (1) a wall surrounding a compartment, the wall comprising at least in part a semipermeable polymeric composition permeable to the passage of fluid and substantially impermeable to the passage of glipizide; (2) a pharmaceutically acceptable composition in the compartment comprising about 2.0 ng to 750 mg of hypoglycemic glipizide for performing an antidiabetic program; (3) a hydrogel composition in the compartment comprising a poly(ethylene) oxide having a 4,000 to 7,500,000 molecular weight for imbibing and absorbing fluid for pushing the glipizide composition from the dosage form; and, (4) at least one passageway in the wall for releasing glipizide; (B) imbibing fluid through the semipermeable wall at a rate determined by the permeability of the semipermeable wall and the osmotic pressure gradient across the semipermeable wall causing the hydrogel composition to expand and swell; and (C) delivering the beneficial glipizide from the dosage form through the exit passage to the warm blooded animal over a prolonged period of time to produce the desired hypoglycemic effect.

Another dosage form administered according to the method of the invention comprises the steps of: (A) admitting into a patient in need of glipizide therapy a dosage form comprising: (1) a wall surrounding a compartment, the wall comprising a semipermeable composition permeable to the passage of fluid and substantially impermeable to the passage of glipizide; (2) a glipizide pharmaceutically acceptable composition in the compartment comprising 2.0 ng to 750 mg of hypoglycemic glipizide for performing an antidiabetic program; an expandable, push composition in the compartment comprising a carboxymethylcellulose having a 200,000 to 1,000,000 molecular weight for imbibing and absorbing fluid for pushing the glipizide composition from the dosage form; and, (4) at least one passageway in the semipermeable causing the expandable composition to expand and push the glipizide composition from the dosage form; and (C) delivering the glipizide at a rate of 10 ng to 25 mg per hour over a period of 2 to 24 hours from the dosage form through the exit port to produce the desired hypoglycemic effect.

The glipizide can be administered by administering a dosage form comprising a semipermeable wall that surrounds a compartment housing a composition comprising glipizide and an osmotic effective solute that imbibes fluid through the semipermeable wall into the compartment thereby causing the glipizide to be pumped through the exit port at a rate controlled by the dosage form at 10 ng to 25 mg per hour over an extended period up to 24 hours.

The method comprises further administering glipizide from a dosage form comprising a diffusion-releasing polymer that release glipizide from a polymer glipizide matrix or through a polymer from a glipizide reservoir at a diffusion controlled-rate of administration over an extended time. The method comprises also administering glipizide at a bioerodable controlled rate and at an ion-exchange controlled-rate over an extended period of time.

In summary, it will be appreciated that the present invention contributes to the art an unexpected and unforseen dosage form that possesses the practical utility for administering aqueous insoluble glipizide from a dosage form at a dose metered release rate per unit time. While the invention has been described and pointed out in detail with reference to operative embodiments thereof it will be understood that those skilled in the art that various changes, modifications, substitutions and omissions can be made without departing from the spirit of the invention. It is intended, therefore, that the invention embrace those equivalents within the scope of the claims which follow.

We claim:

1. A method for treating hyperglycemia in a patient, wherein the method comprises administering to the patient a dosage form comprising 2.0 mg to 750 mg of a glipizide composition that is administered at a dose of 10 ng to 25 mg per hour over an extended period of 24 hours, and wherein the method is characterized by administering the glipizide from a dosage form selected from the group consisting of an osmotic dosage form comprising a semipermeable polymer permeable to the passage of fluid, and a diffusion dosage form comprising a polymer that permits diffusion of glipizide through the polymer.

2. A method for lowering blood sugar in the treatment of a diabetic patient, which method comprises orally administering to the patient an effective blood sugar lowering dose of a composition comprising glipizide and a pharmaceutically acceptable carrier, which blood sugar lowering dose is administered by a method selected from the group consisting of osmosis comprising a semipermeable membrane, diffusion through a polymer permeable to glipizide, and ion-exchange over time to produce the intended lowering of the blood sugar in the patient.

* * * * *